United States Patent [19]
Braig et al.

[11] Patent Number: 5,296,706
[45] Date of Patent: Mar. 22, 1994

[54] SHUTTERLESS MAINSTREAM DISCRIMINATING ANESTHETIC AGENT ANALYZER

[75] Inventors: James R. Braig, Oakland, Calif.; Daniel S. Goldberger, Boulder, Colo.; Mark L. Yelderman, Plano, Tex.; Roger O. Herrera, Oakland, Calif.

[73] Assignee: Critikon, Inc., Tampa, Fla.

[21] Appl. No.: 985,793

[22] Filed: Dec. 2, 1992

[51] Int. Cl.⁵ .................................................. G01J 5/2
[52] U.S. Cl. ................................. 250/339; 250/343; 250/345; 128/719
[58] Field of Search ................. 250/339, 343, 345; 356/246, 446; 128/719; 374/133, 181

[56] References Cited

U.S. PATENT DOCUMENTS

| | | | |
|---|---|---|---|
| 4,692,621 | 9/1987 | Passaro et al. | 250/343 |
| 4,722,612 | 2/1988 | Junkert et al. | 374/124 |
| 4,772,790 | 9/1988 | Aldridge | 250/343 |
| 4,907,166 | 3/1990 | Corenman et al. | 364/497 |
| 4,914,719 | 4/1990 | Conlon et al. | 250/339 |
| 5,046,018 | 9/1991 | Flewelling et al. | 364/497 |
| 5,067,492 | 11/1991 | Yelderman et al. | 128/719 |
| 5,081,998 | 1/1992 | Yelderman et al. | 128/664 |
| 5,095,913 | 3/1992 | Yelderman et al. | 128/719 |

FOREIGN PATENT DOCUMENTS

WO90/04164  4/1990  PCT Int'l Appl.

OTHER PUBLICATIONS

Haaland, David M., "Methods to Include Beer's Law Nonlinearities in Quantitative Spectra Analysis", Computerized Quantitative Infrared Analysis, ASTM STP934, GL McLore Editors, American Society for Testing and Materials, Philadelphia, 1987, pp. 78–94.

*Primary Examiner*—Carolyn E. Fields
*Assistant Examiner*—Drew A. Dunn
*Attorney, Agent, or Firm*—Woodcock, Washburn, Kurtz, Mackiewicz & Norris

[57] ABSTRACT

An anesthetic agent analyzer having six or more independent analytical channels, where each channel comprises a first thermopile which receives incident infrared radiation and a second thermopile behind the first thermopile which is blocked from the incident infrared radiation and thus serves as a reference for detecting ambient temperature variations. The first and second thermopiles are connected in a "parallel opposed" fashion so that the effects of ambient temperature variations automatically cancel and the detectors may be readily configured in a detector package. The anesthetic agent analyzer of the invention is designed for use with a wideband infrared radiation source so that anesthetic agents having characteristic absorption bands in the far infrared wavelength range (6–15 microns) may be more readily detected and discriminated. When implemented in a mainstream configuration, a disposable airway adapter with windows formed of polypropylene or some other suitable window material which minimally attenuates the infrared energy at the wavelengths of interest is also used. The concentrations of the discriminated anesthetic agent gases are then calculated using a second order polynomial equation having cross product terms. By connecting the first and second thermopiles in a back to back configuration, the detector device of the invention permits twice as many independent analytical channels to be provided in the same substrate area, with the resultant reduction in ambient temperature gradients.

20 Claims, 8 Drawing Sheets

SHUTTERLESS MAINSTREAM DISCRIMINATING ANESTHETIC AGENT ANALYZER

BACKGROUND OF THE INVENTION

1. Field of the Invention

The present invention relates to an anesthetic agent analyzer for determining the amount of carbon dioxide, nitrous oxide and other anesthetic agents contained in the respiratory gas of an anesthetized patient. More particularly, the present invention relates to a multi-channel mainstream anesthetic agent analyzer which measures the partial pressures of constituent gases in a respiratory gas stream without using any moving parts and displays the representative gas information on a display.

2. Brief Description of the Prior Art

It is frequently of critical importance to monitor the concentration of carbon dioxide ($CO_2$) in the gases inspired and expired to/from a patient under anesthesia, for expired $CO_2$ concentration is a reliable indicator of the carbon dioxide concentration in the arterial blood. In a clinical setting, monitoring expired $CO_2$ prevents malfunctions in anesthesia rebreathing apparatus from going undetected and delivering excessive amounts of $CO_2$ to the patient. Rebreathing of anesthetic gases is very cost effective and environmentally desirable, but accurate $CO_2$ concentrations are difficult to maintain in the patient circuit without a concentration monitor.

Numerous $CO_2$ concentration monitors have been described in the prior art which direct infrared radiation through a sample of a gaseous mixture and measure the incident radiation illuminating a detecting device, thereby obtaining a measure of the infrared absorption of the $CO_2$ gas. Electrical signals produced by the detecting device are indicative of the infrared absorption of the $CO_2$ gas and can be processed to produce an output indicating the concentration of the $CO_2$ component in the gas being analyzed. This type of gas analyzer operates on the principles that $CO_2$ or any other gas being measured exhibits substantially increased absorption characteristics at specific wavelengths in the infrared spectrum and that higher gas concentrations exhibit proportionally greater absorption.

Analysis of the inspired and expired respiratory gases of a patient also provides information regarding the amount of nitrous oxide ($N_2O$) and other anesthetic agents the respiratory gas contains. Anesthetic agents are typically present as a single agent gas or as a mixture of a number of agent gases during transition from one type of agent gas to another. Some of the most common anesthetic agent gases, other than nitrous oxide, are halothane, ethrane, isoflurane, desflurane and sivoflurane. Such agent gases when administered to a patient must be carefully controlled by the anesthesiologist because of the great risk of supplying too much or too little agent gas.

Previously, the gas analyzers that were used to measure agent gases were not the same devices that were used to measure end-tidal $CO_2$ and $N_2O$. These devices have included mass spectrometers and non-dispersive infrared gas analyzers. Mass spectrometers that are used for such gas measurements are usually part of operating room suites in which one spectrometer is shared among many rooms to measure a multiplicity of gases. However, a mass spectrometer has the disadvantages of cost, maintenance and calibration requirements, slow response time, and non-continuous measurement. Infrared gas analyzers, on the other hand, have the ability to measure the concentrations of inspired and end-tidal $CO_2$ and $N_2O$ in real-time. Prior art nondispersive infrared gas analyzers have also included features for making $CO_2$ and $N_2O$ cross-channel detection as well as temperature and collision broadening corrections to their partial gas pressure measurements. Some of these corrections have been made automatically by the analyzers, while others have been made manually by the operator.

Such non-dispersive infrared gas analyzers generally have two configurations. The first type, and more common, is the sampling or side-stream type which diverts a portion of the patient's respiratory gas flow through a sample tube to the infrared analyzer. The second type, or mainstream type, mounts on the patient's airway and uses a portion of the airway as the sample chamber. A mainstream gas analyzer is often desirable since a sampling system with its pumps and filters and the like is not necessary, thereby substantially reducing the cost of the device. The present invention is directed to such a mainstream infrared gas analyzer, although those skilled in the art will appreciate that the techniques of the invention may also be used with a sidestream configuration such as that described in a commonly owned patent application to Braig, et al., U.S. patent application Ser. No. 07/976,145 filed Nov. 10, 1992.

In typical infrared gas analyzers, the wavelength band of the beam of infrared energy passing through a sample cell containing the unknown gas mixture or through a portion of the main airway is changed periodically by the interposition of one or more filters in the path of the light beam. Typically, this is accomplished by providing a rotating filter wheel containing a plurality of filters which each pass only that radiation in a narrow band corresponding to a characteristic absorption wavelength of a particular gas of interest. Another filter may also be used as a reference filter at a wavelength band close to but not substantially overlapping the characteristic absorption wavelength band of any of the gases present in the sample cell or in the expired air in the mainstream airway. Gas analyzers with such filter wheels are described by Passaro et al. in U.S. Pat. No. 4,692,621; by Conlon et al. in U.S. Pat. No. 4,914,719; by Williams in WO 90/04164; and by Flewelling et al. in U.S. Pat. No. 5,046,018. Such infrared gas analyzers also commonly use a chopper wheel for chopping at a predetermined frequency the infrared light passing through openings in the sample cell or mainstream airway and a source aperture aligned with the reference cell and gas pathway. The chopped light passes through the openings in the detector aperture aligned with a reference cell in the gas pathway to the remaining portions of the assembly so as to provide synchronization for subsequent processing. Such a multi-channel gas analyzer is described, for example, by Corenman et al. in U.S. Pat. No. 4,907,166.

Gas analyzers of the type described in the aforementioned patents usually continuously reference the radiation detected in the characteristic bands to radiation detected at reference levels (i.e., a non-absorbed wavelength with a dark or totally blocked level). By doing so, the effect of drift is minimized and the effect of background noise is reduced. As known to those skilled in the art, drift can occur as a result of contamination on the windows in the sample cell or in the windows of the mainstream airway adapter which will attenuate the radiation passing therethrough and which can be interpreted erroneously to indicate the presence of the gas to be detected in the gas sample. Drift can also be caused by shifts in the output of the detector and temperature changes in the source of the infrared radiation.

Another source of error for infrared gas analyzers is the presence of certain gases or combinations of gases in the measured airstream or sample cell which have absorption bands which substantially overlap. This is undesirable, for there are instances where the gases that need to be measured simultaneously have very significantly overlapping absorption bands in the infrared range. A well-known example is the case of the anesthetic halocarbons: halothane, ethrane (or enflurane), and isoflurane. These three gases, which are hydrocarbon derivatives, have relatively weak absorption bands bunched together in the 3.3–3.5 micron (middle infrared) range, much like other hydrocarbons, and thus have modulations in the middle infrared range which are hardly sufficient for a useful measurement. This leads to poor sensitivity, a bulky sample chamber, and vulnerability to interference from other gases. However, as will be noted in more detail below, these gases also have strong but overlapping absorption bands in the far infrared range (beyond the 3.3–3.5 micron range) extending all the way up to 15 microns. Since these anesthetic hydrocarbon derivatives have much stronger absorption in the 6–15 micron (far infrared) range, it is desired to develop a measuring instrument which can measure the absorption of infrared light in the 6–15 micron (far infrared) range, despite the overlapping characteristics of the absorption bands of the halocarbons at these wavelengths.

Accordingly, the present invention is intended to measure the concentrations of the anesthetic agents in the far infrared wavelength range so as to provide a more precise measurement of the concentrations of these anesthetic agents than has previously been possible. It is also desired to develop an anesthetic agent analyzer which, unlike the above-mentioned devices, has no moving parts and is relatively inexpensive. In particular, an anesthetic agent analyzer is desired which can measure the concentration of anesthetic agents in the far infrared wavelength range in a system which does not use rotating filter wheels or choppers as in the aforementioned prior art patents.

Infrared gas analyzers have previously been described which do not require a motor driven chopper wheel or rotating filter wheel for its operation. For example, Aldridge discloses in U.S. Pat. No. 4,772,790 an optical gas analyzer which uses thermopiles as optical detectors. The thermopiles are formed of an array of interconnected thin films deposited on a heat insulative substrate to form a multitude of thermocouples. The array is configured such that infrared light impinges upon a number of the thermocouples, while the remainder of the thermocouples are shielded from the infrared light and employed to compensate each thermopile output signal for changes in ambient temperature. Similarly, Junkert et al. disclose in U.S. Pat. No. 4,722,612 an infrared thermometer which shields one thermopile from the incident infrared radiation and uses its output to compensate for changes in ambient temperatures. Of course, both of these detectors require close matching between the detecting thermopiles and the "shielded" thermopiles in order to prevent mismatch errors.

Another infrared gas analyzer which does not require a motor driven chopper wheel or filter wheel for its operation is described by the present inventors in U.S. Pat. Nos. 5,081,998 and 5,095,913, which are also assigned to the present assignee. The present inventors therein describe an optically stabilized, shutterless infrared capnograph which provides the absolute concentrations of the constituents of the respiratory airstream of a patient without the thermal drift problems normally associated with thermopile detectors. The detector described in these patents eliminates the need for a mechanical shutter to modulate the incident infrared beam and the need for a modulated source by providing a unique arrangement whereby paired thermopiles are connected in series opposition to each other and are preceded by an analytical reference filter for passing a desired wavelength. A neutral density filter is also placed in the optical path of one of the thermopiles in the pair to attenuate the incident light, and the difference between the outputs of the thermopiles is used to eliminate the effects of background thermal noise so as to increase the reliability and response time of the device.

As illustrated in FIG. 1, such an optically stabilized infrared energy detector comprises a pair of thermopile detectors 100 and 102 which are connected in series opposed relation to each other. As shown, while infrared light impinges upon both of the infrared detectors 100 and 102, reference element 102 is disposed behind a neutral density filter (as shown by phantom outline) which attenuates a portion of the incident infrared radiation. As a result of this arrangement, the background temperature effects equally affect both detectors 100 and 102 and cancel when the outputs are summed. The sum output of operational amplifier 104 is thus unaffected by variations in ambient temperature and the like.

An exploded view of an optically stabilized infrared energy detector is shown in FIG. 2. As shown, the optically stabilized infrared energy detector 200 comprises an aperture 202 which is placed over analytical filters 204 including $CO_2$ filter 206, $N_2O$ filter 208 and a reference filter 210. A neutral density filter (not shown) is also placed over one channel of each analytical filter 204. Two substrate layers 212 preferably formed of antimony and bismuth are then placed on either side of a thin film thermopile layer 214 which includes thermopiles for detecting the incident infrared energy which has passed through the apertures 202, the analytical filters 204, the neutral density filter, and the openings in the substrates 212 so as to impinge upon the respective thermopiles in thermopile layer 214. A foil background 216 is also provided on the back of the lower substrate 212 so as to prevent the impingement of infrared energy from the back of the detector 200 onto the thermopiles of thermopile layer 214. A bead thermistor 218 is also provided behind foil 216 to measure the absolute substrate temperature for use in computing the ratio between the incident signals after cancellation of thermal effects. The entire assembly is then placed upon a header assembly 220 via header pins 222 as illustrated.

The optically stabilized infrared energy detector illustrated in FIG. 2 incorporates six coplanar detector channels, three of which serve as reference channels and three of which serve as analytical channels. As shown in FIG. 1, each reference detector in a reference channel is connected to its analytical partner in a series opposed configuration. It is desired to modify this configuration such that all six of the illustrated channels may be used as independent analytical channels, thereby permitting three or more additional anesthetic agents such as ethrane, halothane, and isoflurane to be detected with the same thermopile layer 214. However, it was discovered by the present inventors that the system of FIGS. 1 and 2 had to be substantially geometrically reconfigured into a new topography in order to permit six or more independent analytical channels to be used with a comparable thermopile assembly. As will be described in detail below, a new topography has accordingly been developed in accordance with the present invention.

Accordingly, a discriminating anesthetic agent analyzer is desired which has no moving parts and thus overcomes the problems of the aforementioned prior art agent analyzers and which is small, inexpensive and simple to operate. A discriminating anesthetic agent analyzer is also desired which is light in weight and durable so that it may be used in a mainstream configuration. An anesthetic agent analyzer is further desired which is accurate and which does not require excessive calibration. In addition, a discriminating anesthetic agent analyzer is desired which improves upon the topography of the above-mentioned optically stabilized infrared energy detector so that more analytical channels may be disposed in the same relative area. The invention described herein has been designed to meet these needs.

SUMMARY OF THE INVENTION

The present invention meets the above-mentioned needs in the art by providing a shutterless discriminating anesthetic agent analyzer which has a new topography which allows up to eight channels to be used as independent analytical channels for detecting the absorption of infrared light at predetermined wavelengths. In a preferred embodiment, identical thermopiles are located "behind" thermopiles which are in the path of the incident light, and the thermopiles which are not in the path of the incident light are shielded therefrom so as to provide reference outputs. The reference thermopiles and the thermopiles in the path of the incident light are preferably connected back to back in "parallel opposed" fashion so that the construction of the infrared detector may be greatly simplified while providing multichannel detection.

In particular, the present invention relates to a device for simultaneously measuring the concentrations of respective anesthetic agents in a respiratory gas stream of a patient. Such a detection device in accordance with a preferred embodiment of the invention preferably comprises a source of infrared radiation, a separate infrared detector for each of the respective anesthetic agents which is disposed so as to receive incident radiation from the infrared radiation source and to produce first electrical signals representative of the received incident radiation and ambient temperature transients, means for directing at least a portion of the respiratory gas stream between the infrared detectors and the infrared radiation source, a separate reference infrared detector for each of the infrared detectors which is connected in a parallel opposed manner with its corresponding infrared detector so as to output second electrical signals representative of ambient temperature transients, means for shielding the reference detectors from the infrared radiation source, and means for processing the first and second electrical signals to produce signals representative of the concentrations of the respective anesthetic agents. The detectors of the invention are preferably configured so that each reference infrared detector and its corresponding infrared detector are comprised of thermopiles and are disposed back to back with shielding means such as aluminum foil therebetween.

Preferably, the infrared radiation source is a black body source having an operating temperature which is approximately 350° C. and which emits a detectable amount of infrared radiation at wavelengths from 2–13 microns. In a preferred embodiment, the invention further includes an analytical filter for each of the anesthetic agents, each analytic filter passing to the corresponding detector incident infrared energy in a narrow band about an infrared frequency which is readily absorbed by the corresponding anesthetic agent. For example, the analytic filters in a preferred embodiment pass anesthetic agents such as isoflurane, ethrane and halothane. For such an embodiment, the analytical filters preferably comprise a filter with a narrow band about approximately an 8.2 micron wavelength for isoflurane, a filter with a narrow band about approximately an 8.6 micron wavelength for ethrane, and a filter with a narrow band about approximately a 12.4 micron wavelength for halothane. However, those skilled in the art will appreciate that anesthetic agents such as sivoflurane and desflurane may also be detected so long as the appropriate filters are used. In addition, the anesthetic agent detector of the invention may further include channels for detecting carbon dioxide and nitrous oxide.

The directing means of the invention preferably comprises an airway adapter which is inserted into a patient's respiratory airway so as to receive the patient's exhaled airstream. In a preferred embodiment, the airway adapter is formed of disposable plastic and includes plastic windows in an optical path between the infrared detectors and the infrared radiation source. For optimum transmission characteristics, the airway adapter is ideally formed of a polycarbonate or polyester and includes polypropylene windows in the optical path between the infrared detectors and the infrared radiation source.

The processing means of the invention ideally processes the first electrical signals D and the second electrical signals R to determine the concentration $A_X$ of three respective anesthetic agents X in accordance with the following equation:

$$A_X = A_3 C_a + A_2 C_b + A_1 C_c + A_3 A_2 C_d + A_3 A_1 C_e e + 1 A_2 C_f + A_3^2 C_g + A_2^2 C_h + A_1^2 C_i,$$

where $A_n = D_n/R_n$ and where $C_a - C_i$ are respective calibration coefficients. This Equation corrects for collision broadening, non-linearities and other errors which may be introduced into the detected signal.

The scope of the invention also includes a method of simultaneously measuring the concentrations of respective anesthetic agents in a respiratory gas stream of a patient. Such a method in accordance with a preferred embodiment of the invention comprises the steps of:

transmitting a beam of infrared radiation through the respiratory gas stream;

detecting the intensity of the infrared radiation, after it has passed through the respiratory gas stream, using a separate infrared detector for each of the respective anesthetic agents, and generating first electrical signals representative of the detected infrared radiation;

detecting ambient temperature transients in a region adjacent the infrared detectors using a separate reference infrared detector adjacent each of the infrared detectors, each reference detector being connected in parallel opposed manner with its corresponding infrared detector and being shielded from the infrared radiation, and generating second electrical signals representative of the ambient temperature transients;

generating difference signals respectively corresponding to the differences between the respective first electrical signals and second electrical signals; and processing the difference signals to produce signals representative of the concentrations of the respective anesthetic agents.

In accordance with the method of the invention, the transmitting step preferably comprises the step of emitting a detectable amount of infrared radiation at wavelengths from 2-13 microns from a black body source having an operating temperature which is approximately 350° C. A preferred embodiment of the method further includes the steps of filtering the infrared radiation after it has passed through the respiratory gas stream using separate analytical filters for each of the anesthetic agents, each analytical filter passing incident infrared energy in a narrow band about an infrared frequency which is readily absorbed by the corresponding anesthetic agent.

The scope of the invention further includes an infrared energy detector for measuring the amount of incident infrared radiation received from a source of infrared energy. Such an infrared energy detector in accordance with a preferred embodiment of the invention preferably comprises a plurality of thermopile detectors disposed so as to receive incident radiation from the infrared radiation source via respective optical channels and to produce first electrical signals representative of the received incident radiation and ambient temperature transients, a separate reference thermopile detector for each of the thermopile detectors which is connected in parallel opposed manner with its corresponding thermopile detector and which outputs second electrical signals representative of ambient temperature transients, and means for shielding the reference thermopile detectors from the infrared energy source. Preferably, the detector of the invention further comprises a separate analytical filter over each of the thermopile detectors so as to form respective optical channels, where each analytic filter passes incident infrared energy in a narrow band about an infrared frequency which is readily absorbed by a particular gas component with a characteristic absorption band centered about the infrared frequency. In a preferred embodiment, each reference thermopile detector and its corresponding thermopile detector are comprised of thermopiles which are disposed back to back with shielding means such as aluminum foil therebetween.

BRIEF DESCRIPTION OF THE DRAWINGS

The objects and advantages of the invention will become more apparent and more readily appreciated from the following detailed description of presently preferred exemplary embodiments of the invention taken in conjunction with the accompanying drawings, of which.

DETAILED DESCRIPTION OF THE PRESENTLY PREFERRED EMBODIMENT

A shutterless discriminating anesthetic agent analyzer with the above-mentioned beneficial features in accordance with a presently preferred exemplary embodiment of the invention will now be described with reference to FIGS. 3–10. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

Figure 1:
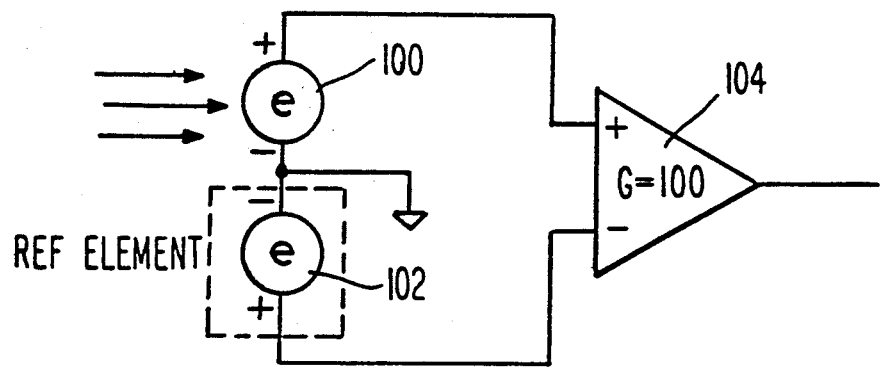
FIG. 1 illustrates the series opposed connection of prior art optically stabilized infrared energy detectors.
Figure 2:
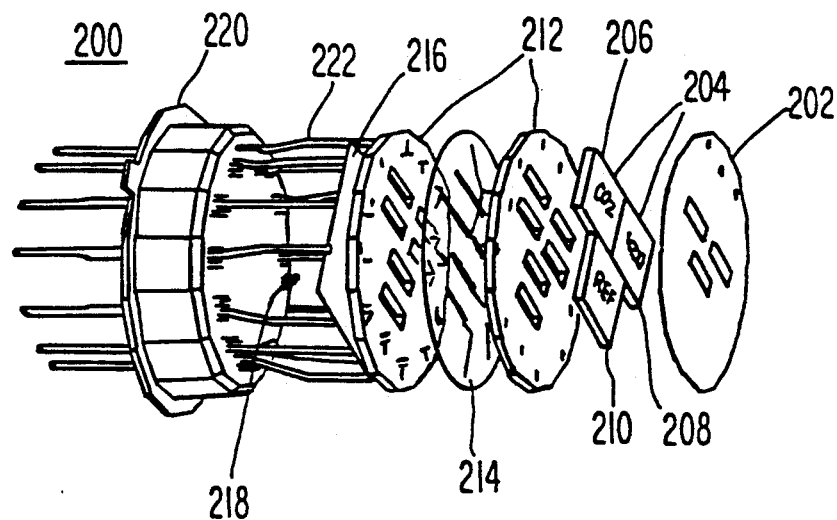
FIG. 2 is an exploded view of a prior art optically stabilized infrared energy detector.

As noted above with respect to FIGS. 1 and 2, the optically stabilized thermopile detector 200 incorporates six coplanar detection channels, three of which serve as references. As illustrated in FIG. 2, this construction provides separate analytical channels for measuring $CO_2$, $N_2O$ and a reference gas. In the illustrated three channel design, the reference thermopile is connected to its analytical partner in a "series opposed" configuration so that transient effects automatically cancel. It is desired to extend such a design so that the concentration of anesthetic agents such as ethrane, halothane, and isoflurane provided to a patient under anesthesia may also be measured using the same detector used to measure $CO_2$ and $N_2O$. For this purpose, the present invention has a new topography in which all six channels of the detector illustrated in FIG. 2 may be used as independent analytical channels. This is accomplished by providing six identical reference thermopiles "behind" the thermopiles in the path of the incident infrared radiation, shielding the reference thermopiles from the incident infrared radiation, and then connecting respective pairs of thermopiles such that background effects cancel. As will be described in detail below, the present inventors have discovered that in order to do this the geometry of the detector had to be substantially redesigned and the detectors connected in a "parallel opposed" fashion.

Figure 3:
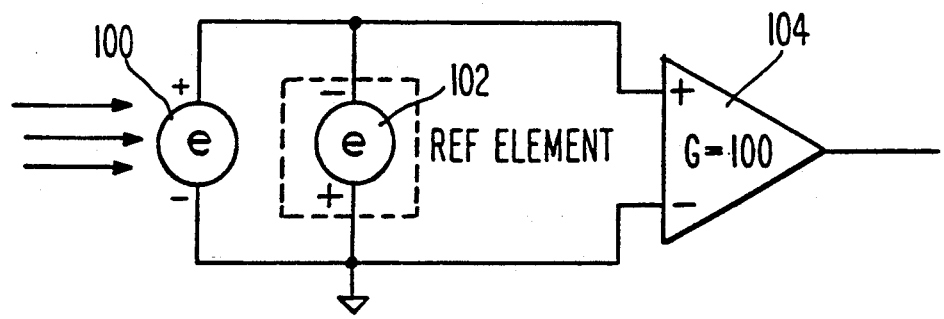
FIG. 3 illustrates the "parallel opposed" connection of the thermopiles of the infrared energy detector in accordance with the invention.

FIG. 3 illustrates the detector arrangement of the invention whereby the thermopile in the path of the incident infrared radiation is connected in a "parallel opposed" fashion with its associated reference thermopile 102, which is shielded from the incident infrared radiation as shown in phantom. As in the embodiment of FIG. 1, the outputs of thermopiles 100 and 102 are provided to operational amplifier 104 which provides an output independent of ambient temperature variations. Those skilled in the art will appreciate that because of the parallel connection of thermopiles 100 and 102 in the embodiment of FIG. 3 the detector of the invention will have a responsivity which is approximately one-half that of the series connected three channel detector illustrated in FIG. 2. However, despite this reduction in responsivity, the present inventors have discovered that highly accurate anesthetic agent concentration readings may be obtained using the detector of the invention. Such a detector for use in an anesthetic agent analyzer in accordance with a preferred embodiment of the invention will now be described with reference to FIGS. 4 and 5.

Figure 4:
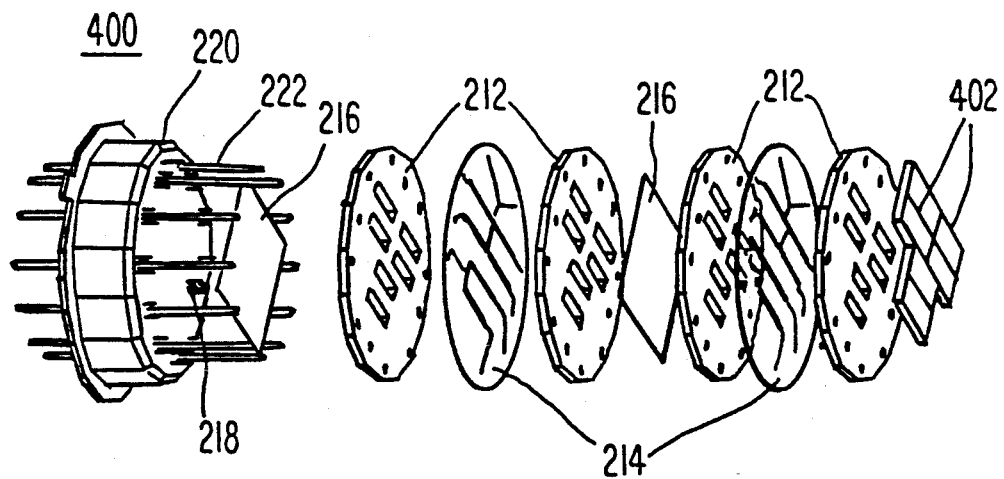
FIG. 4 is an exploded view of a preferred embodiment of a six channel detector for an anesthetic agent analyzer in accordance with the invention.

FIG. 4 illustrates a six channel detector 400 for an anesthetic agent analyzer in accordance with a preferred embodiment of the invention. As illustrated, the six channel embodiment of FIG. 4 uses 2 similar thermopile assemblies, one located below the other on the header pins 222. The assembly on top serves as the optically sensitive element, while the one below the foil 216 serves as the reference element. As illustrated, the lower assembly is blocked by the upper assembly and by foil 216 from receiving incident energy. In addition, the lower assembly is fabricated with its antimony and bismuth substrate layers 212 reversed from the upper assembly so that the reference element produces a voltage of opposite polarity than the optically sensitive element. In this manner, the respective detectors are readily connected in a "parallel opposed" manner on the header pins 222 on which both assemblies reside. As illustrated in FIG. 4, the same header assembly 220 with header pins 222 and a bead thermistor 218 may be used as in the three channel detector illustrated in FIG. 2. However, as just noted, the detector illustrated in FIG. 4 differs in that the reference detector and the detector in the path of the incident infrared radiation are connected in back to back configuration on the header pins 222 with an additional foil layer 216 therebetween so as to block the reference thermopiles from the incident infrared radiation.

As illustrated in FIG. 4, six different analytical filters 402 are provided over the respective apertures of substrates 212 so as to establish six different analytical channels. This is in marked contrast to the embodiment of FIG. 2 whereby only three analytical channels and three reference channels are provided and the 3 reference channels are covered by an attenuating neutral density filter (not shown) in an optically stabilized configuration.

Those skilled in the art will appreciate that the six channel topography illustrated in FIG. 4 may be readily expanded to eight channels without loss of junctions per detector channel or reduction in line width of the detector elements. However, to increase the analytical channel topography to any more than eight channels would involve either reduction of the number of junctions per element, reduction of processing line widths, or an increase in the overall size and weight of the detector.

Figure 5:
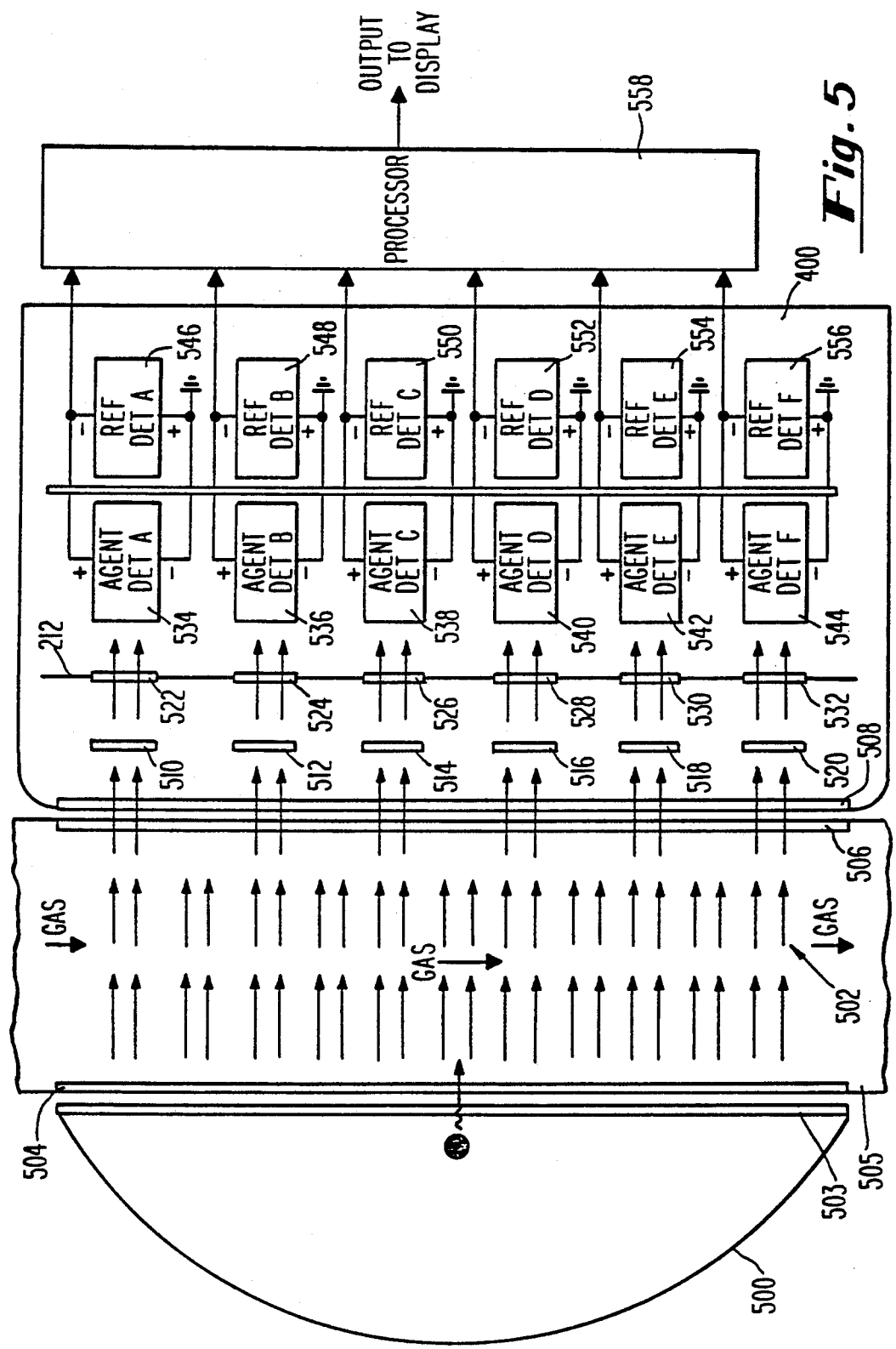
FIG. 5 is a schematic illustration of a detector and its optical path constructed in accordance with the principles of the present invention.

FIG. 5 illustrates the optical path of a preferred embodiment of a detector 400 constructed in accordance with the techniques of the invention. As shown, infrared energy is emitted from wideband infrared radiation source 500, which is preferably a wideband infrared radiation source of the type described in commonly owned U.S. patent application Ser. No. 07/782,990. Infrared energy 502 emitted from infrared source 500 passes through optical window 503 and then through a first optical window 504 of an airway adapter 505. The infrared energy 502 passes through the gas being analyzed and is modulated as it passes through the airway adapter 505. The modulated infrared energy 502 then passes through a second optical window 506 to the detector 400. Preferably, airway adapter 505 is similar to that described in U.S. Pat. No. 5,067,492 (assigned to the same assignee as the present invention) except that the airway adapter is formed of a material with appropriate transmission characteristics as will be described in more detail below.

The airway adapter 505 is preferably connected on the inspired and/or expired airstream of the patient so as to receive respiratory gas including, for example, $CO_2$, $N_2O$ and any anesthetic agent gases provided to the patient under anesthesia. As will be appreciated by those skilled in the art, some of the infrared energy 502 emitted by infrared source 500 is absorbed (modulated) by the gas in the airway adapter 505 which is in the path of the infrared source 500, while the remainder of the infrared energy 502 will pass through second optical window 506 of the airway adapter and then through optical window 508 of the detector 400 before impinging upon a group of filters 510, 512, 514, 516, 518 and 520, which in a six channel embodiment comprise an analytical $CO_2$ filter, an analytical $N_2O$ filter, a reference filter, and three different analytical filters which pass bandwidths associated with three different anesthetic agent gases such as isoflurane, ethrane, and halothane. As will be appreciated by those skilled in the art, the analytical filters are typically bandpass filters which pass narrow bands of energy in wavelength ranges which are readily absorbed by the constituent gases being measured. Preferably, the reference filter is also a bandpass filter which passes a band of energy excluding, for example, those wavelengths readily absorbed by $CO_2$. As will be appreciated by those skilled in the art, the filters and detector channels may be organized in any desired order in the embodiment of FIG. 5.

The infrared energy which has passed through the respective analytical filters 510-520 then passes through respective apertures 522, 524, 526, 528, 530 and 532 to transmit energy only to the areas of the thermopile substrate 214 on which the thermopile detectors are formed. The infrared energy 502 which passes through the respective apertures 522-532 of the substrate 212 then impinges upon respective anesthetic agent detectors A(534), B(536), C(538), D(540), E(542) and F(544) of thermopile layer 214. As in the detector described above with respect to FIGS. 1 and 2, these respective anesthetic agent detectors A-F are preferably thermopile detectors comprising a plurality of thermocouples mounted on the substrate 212 so as to form a hot sensor junction which is within respective apertures 522-532 and a cold, or reference, junction which is blocked by the substrate 212. Most preferably, the thermocouples of the respective anesthetic agent detectors 534-544 are of the type comprising a metallic circuit deposited upon a polyester film, such as Mylar ™, or some other suitable substrate. A preferred embodiment of the invention utilizes thermocouples having a substrate thickness of approximately 1 mil.

As further illustrated in FIG. 5, a foil layer 216 is disposed behind the respective detectors 534-544 so as to block incident infrared radiation from reaching the respective reference detectors A(546), B(548), C(550), D(552), E(554) and F(556). Preferably, as illustrated in FIG. 4, reference detectors A-F are disposed in back to back configuration with the corresponding anesthetic agent detectors A-F which receive the incident infrared radiation 502 which has passed through the respiratory airstream of the patient. As described above, the anesthetic agent detectors A-F and reference detectors A-F are preferably connected in a "parallel opposed" configuration as illustrated in FIG. 3 so that variations in ambient conditions detected by reference detectors A-F may be readily subtracted from the signal output by the respective anesthetic agent detectors A-F. Such a parallel opposed configuration is readily provided by connecting the reference detectors A-F across the header pins 222 and then connecting the corresponding anesthetic agent detectors A-F across the same header pins 222 only with a reversed polarity. The outputs of the respective detectors 534-544 and 546-556 are then input to a processor 558 for determining the concentrations of the respective anesthetic agent gases from the signals provided by the respective detectors using mathematical techniques to be described in more detail below.

As will be appreciated by those skilled in the art, the present invention supplies output signals to processor 558 which are substantially independent of the influence of ambient temperature changes because of the parallel opposed configurations of the detectors. In addition, those skilled in the art will appreciate that by disposing the anesthetic agent detectors A-F and the reference detectors A-F so that they are exposed to the same ambient temperature but only one thermopile in each pair is exposed to incident infrared radiation while the other is shielded from the incident infrared radiation, the ambient temperature effects will cancel for the reasons described by Junkert et al. in U.S. Pat. No. 4,722,612. In particular, the ambient temperature effects will cancel so long as the respective thermopiles in each pair are mounted proximate to one another so as to be exposed to the same ambient temperature, which may be detected, for example, using thermistor 218 as illustrated in FIG. 4. For this purpose, the respective detectors are also preferably formed on respective insulative sheets 214, preferably formed of Mylar ™, which are stretched across and supported on thermally conductive substrates 212. Substrates 212 and Mylar thermopile sheets 214 are then aligned so that the thermopile detectors are placed within the respective apertures 522-532 of the substrates 212. Then, as illustrated in FIG. 4, the substrates 212 are stacked against opposite surfaces of infrared radiation barrier or foil 216 and supported on the header pins 222. As described above, header pins 222 not only support the detectors of the invention but also provide a "parallel opposed" electrical connection to the thermopile devices formed on the Mylar layers 214. By contrast, Junkert et al. use a series opposed configuration to cancel the ambient temperature effects independent of the detector geometry.

Figure 6:
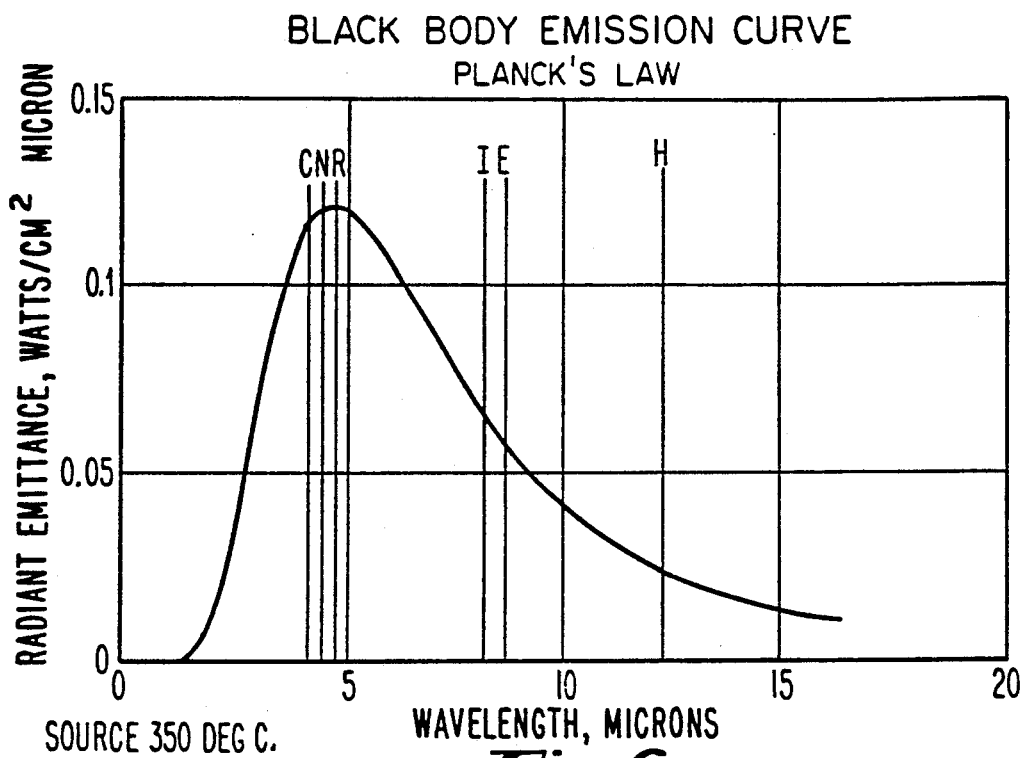
FIG. 6 illustrates a black body emission curve of a preferred embodiment of an infrared source in accordance with the invention.

Infrared source 500 of the invention emits infrared light which obeys Planck's law describing how an ideal emitter (a black body) has a varying radiance with wavelength. FIG. 6 illustrates the emission curve of a black body heated to 350° C. As indicated in FIG. 6, the emittance decreases as the wavelengths increase. The source operating temperature was selected to be near 350° C. so that the emission peak was in the region used for $CO_2$ absorption, making the source very efficient for use in a $CO_2$ analyzer. As known to those skilled in the art, the absorption band of $CO_2$ is preferably centered at 4.256 microns which, as illustrated in FIG. 6, is very close to the peak of a black body heated to 350° C. However, other temperatures may be chosen so that the emission peak is closer to that used for the other anesthetic gases.

While it has heretofore been difficult to design an anesthetic agent analyzer in the far infrared wavelength range (6-15 microns) because of the decreased emission from the source, it is desired in accordance with the present invention to design an anesthetic agent analyzer which operates in the far infrared range because of the better defined absorption spectra of the anesthetic agents in this range. Such an anesthetic agent analyzer has been made possible in accordance with the present invention by using an infrared source 500 with an emission profile such as that illustrated in FIG. 6.

In order to design an anesthetic agent analyzer in the far infrared range, it is necessary for the thermopile detector used to have a relatively flat response in the far infrared range which does not vary with wavelength. Such a flat response means that the detector will not be any less sensitive at the longer wavelengths and will not contribute to reduced signals as does the source emission. The detector assembly of the type described above with respect to FIGS. 4 and 5 has been found to have a relatively flat response which does not vary with wavelength and is thus suitable for use in such a far infrared wavelength anesthetic agent analyzer.

As also will be appreciated by those skilled in the art, another element of the optical system that affects the signal size is the attenuation caused by the infrared transmissive windows 504 and 506 used on the airway adapter 505. It is thus desired to use a material for the transmissive windows 504 and 506 which does not substantially attenuate the infrared energy passing therethrough so that the measured signals have values which are easier to discriminate. Indeed, because long wavelength anesthetic agent signals may have signal levels as low as 15% of the signal level of the $CO_2$ channel, with the resultant proportionately lower signal to noise ratios from the long wavelength channels, it is desired to form the airway adapter of a material with minimal absorption in the far infrared wavelength range.

Figure 7:
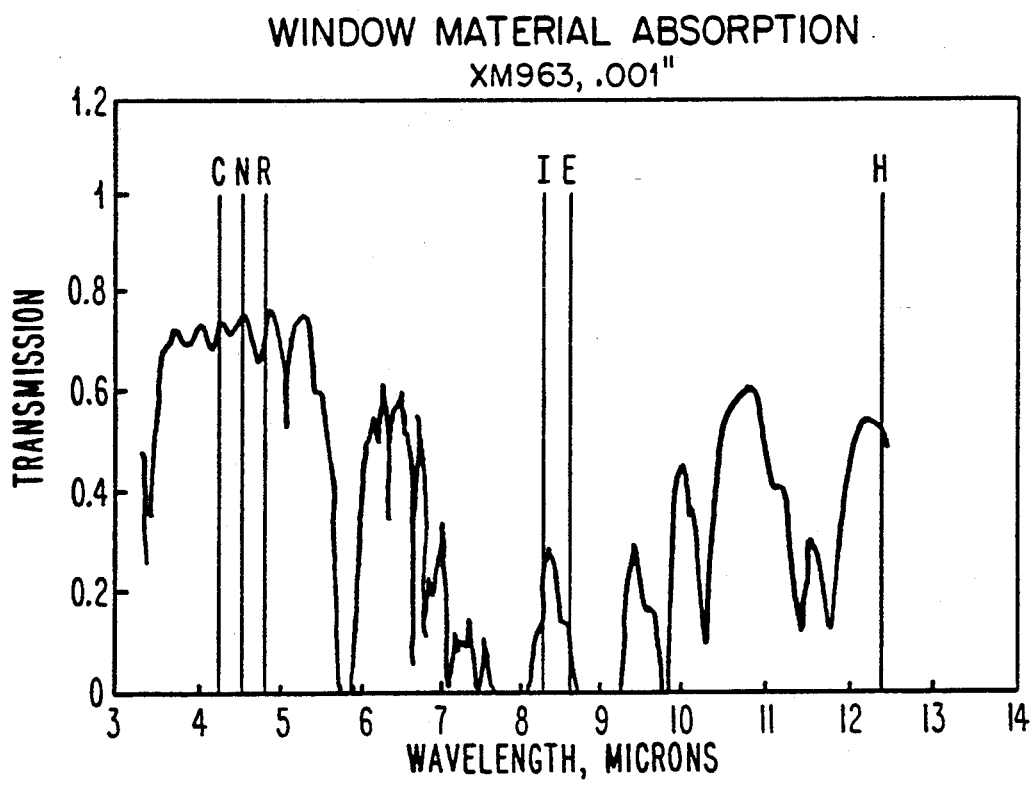
FIG. 7 illustrates the absorption spectra of a polyester window film of an airway adapter of the type described in U.S. Pat. No. 5,067,492.
Figure 8:
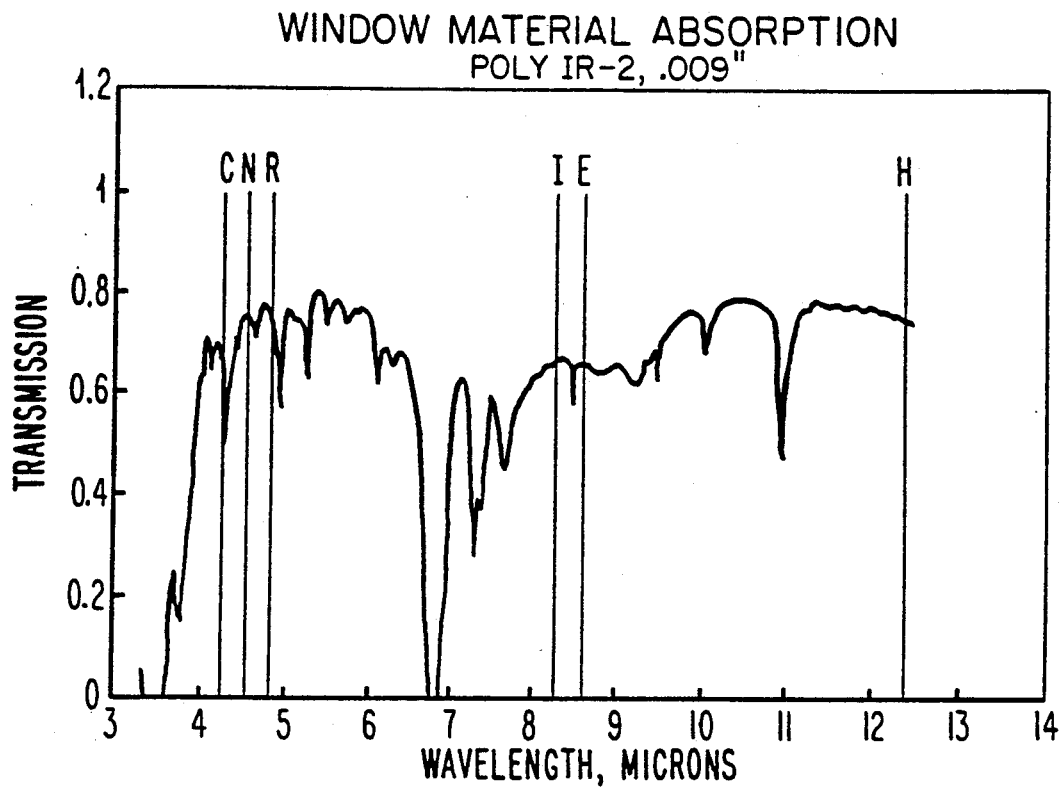
FIG. 8 illustrates the absorption spectra of a window film material provided by Fresnel Technologies, Inc.

As noted above, an airway adapter for use with the anesthetic agent monitor of the invention may be similar to that described in U.S. Pat. No. 5,067,492. The polyester window film used in the airway adapter of that patent was selected for its strength in thin sections and its ability to transmit the infrared wavelengths of interest for the analysis of $CO_2$ and $N_2O$. Unfortunately, as illustrated in FIG. 7, the polyester window film of that airway adapter does not transmit the long infrared wavelengths required for anesthetic agent analysis in accordance with the invention very well. This is shown in the annotated transmission spectra of FIG. 7 by the modulation at lines I, E and H, which represent three typical wavelengths that can be used to monitor the anesthetic agents isoflurane, ethrane and halothane, respectively.

The present inventors have found a plastic material that does a better job of transmitting the long wavelength infrared energies. Such a material is available from Fresnel Technologies, Inc. under the tradename POLY IR-2 and has the absorption spectra illustrated in FIG. 8. As can be appreciated by comparing FIG. 8 with FIG. 7, the POLY IR-2 window material absorbs substantially less infrared energy at the I, E and H wavelengths than the polyester window film illustrated in FIG. 7.

Figure 9:
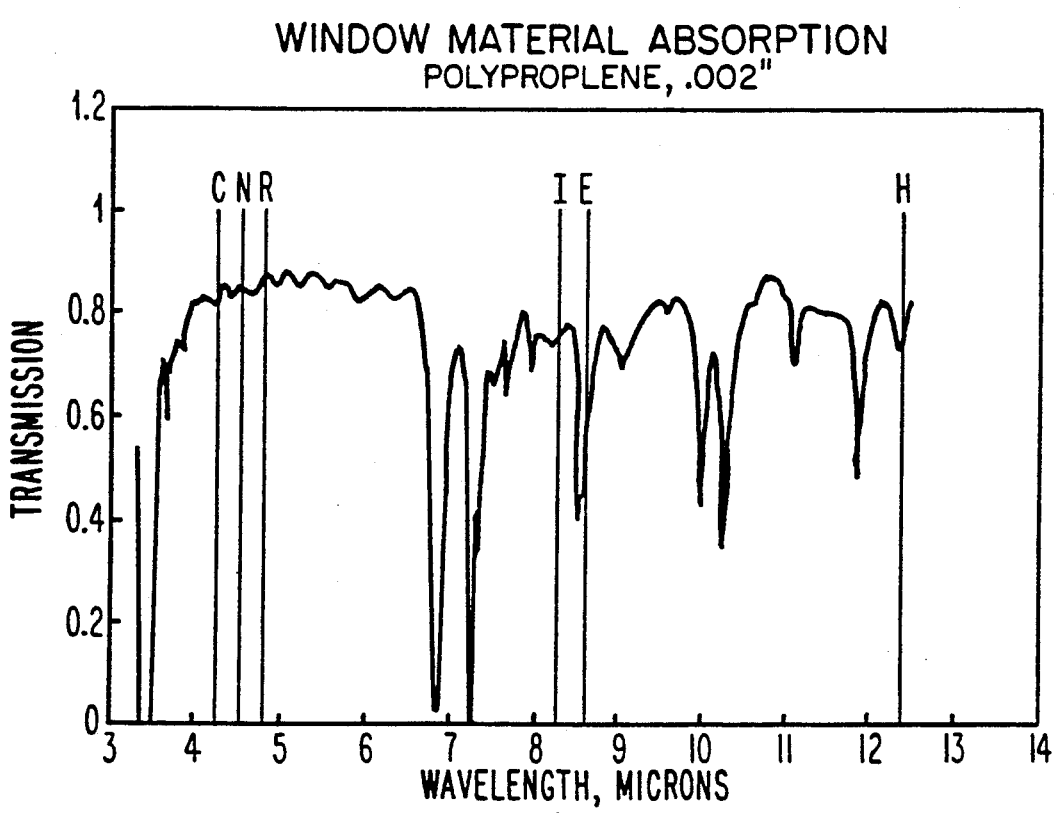
FIG. 9 illustrates the absorption spectra of a polypropylene window material for use in the airway adapter in accordance with a preferred embodiment of the invention.
Figure 10A:
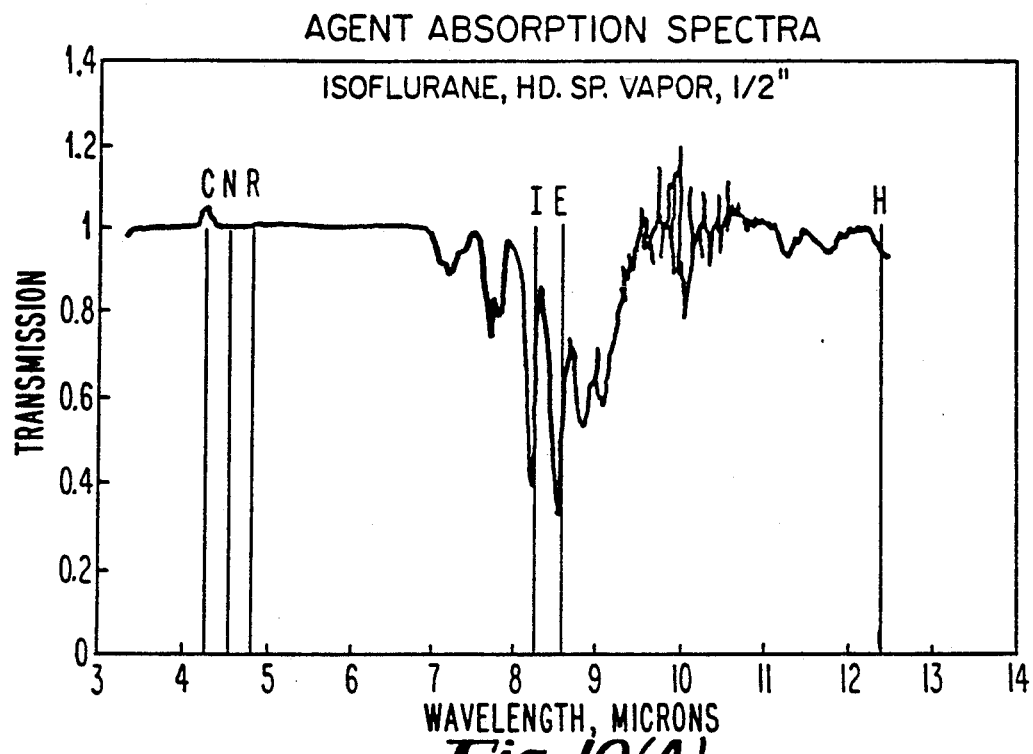
FIGS. 10(A), 10(B), 10(C), 10(D) and 10(E) respectively illustrate the infrared absorption spectra of the anesthetic halogens: isoflurane, ethrane, halothane, desflurane, and sivoflurane.
Figure 10B:
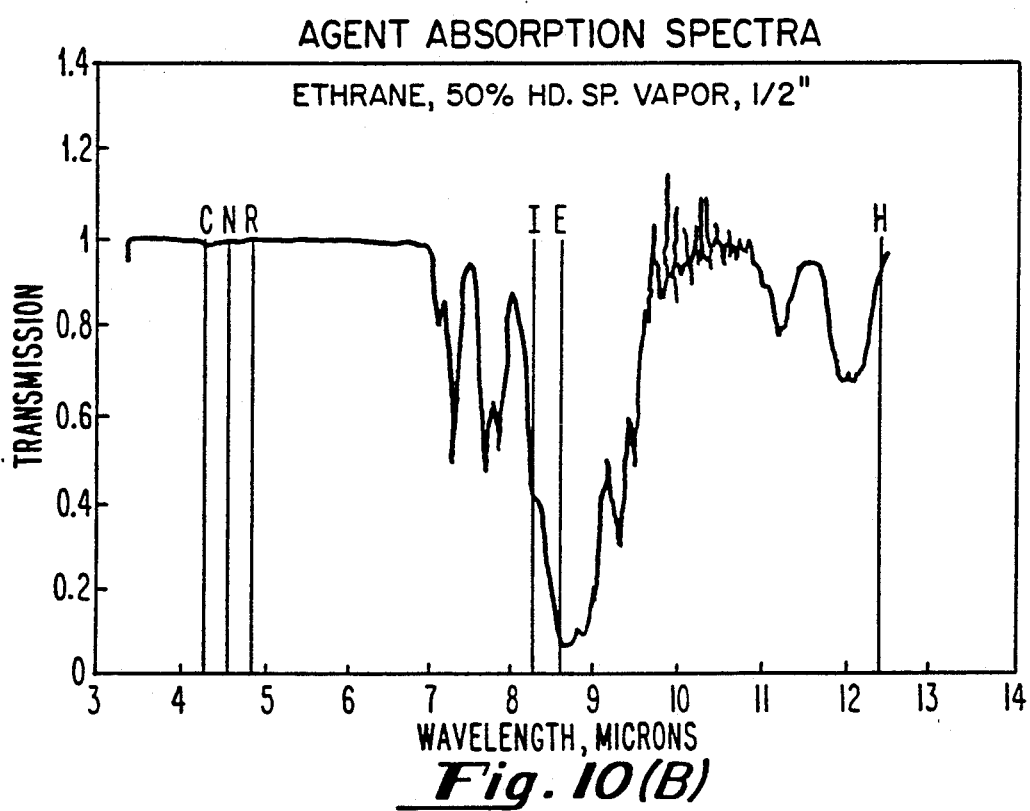
Figure 10C:
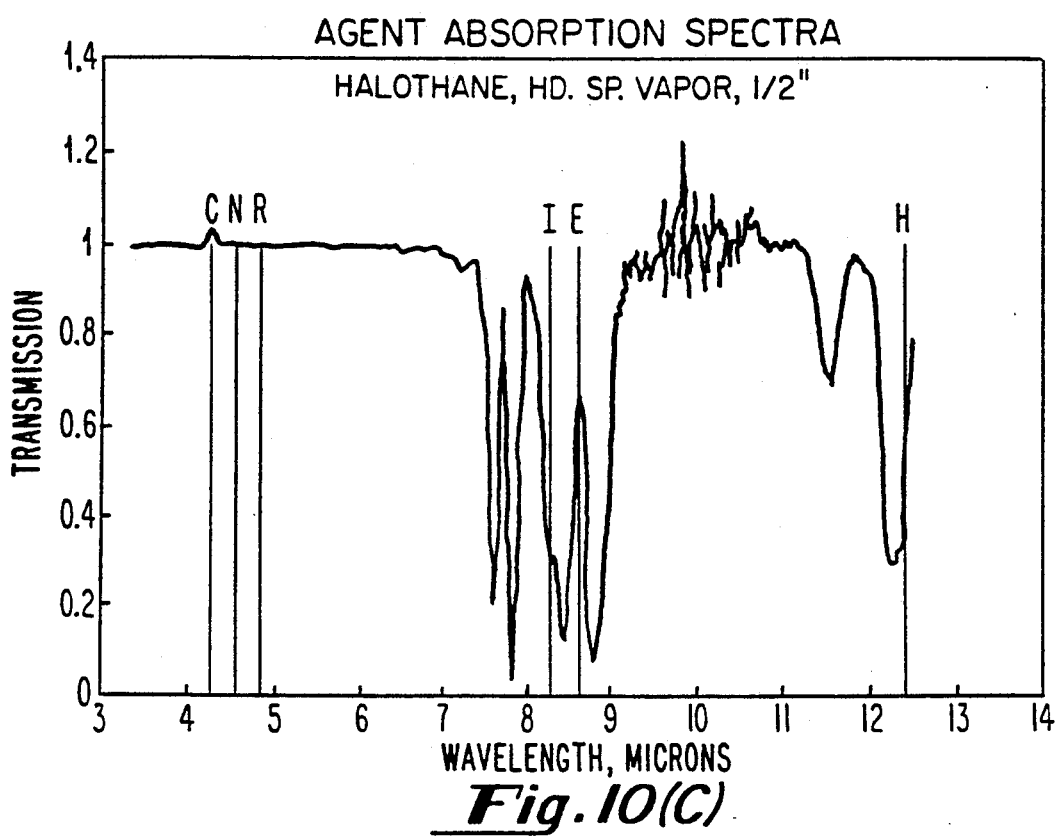
Figure 10D:
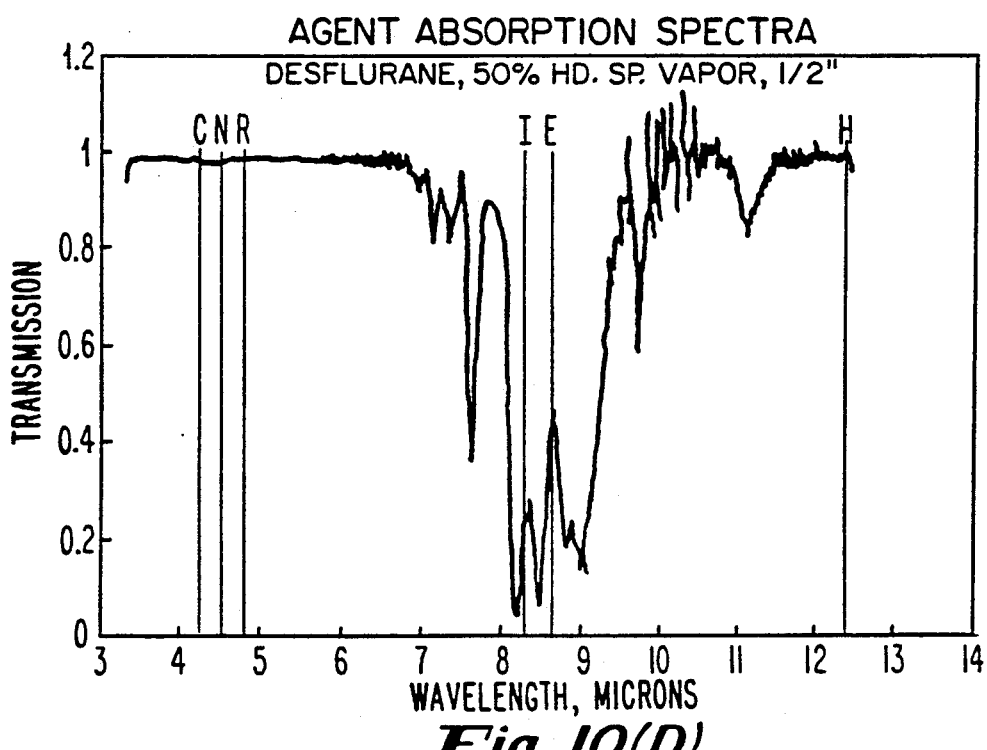
Figure 10E:
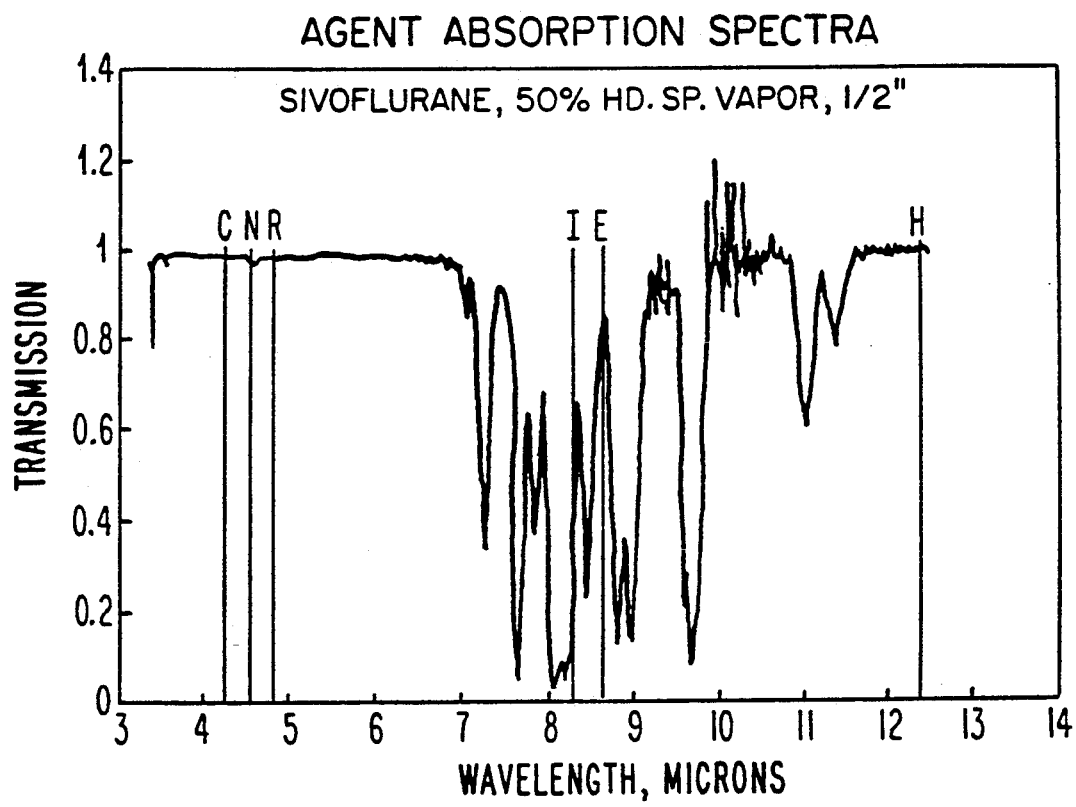

The present inventors have also found that generic polypropylene is another acceptable material for forming the windows of an airway adapter in accordance with the invention. An annotated transmission spectra of polypropylene is shown in FIG. 9. As will be appreciated by those skilled in the art, FIG. 9 illustrates that generic polypropylene also absorbs substantially less infrared energy at the I, E, and H wavelengths than the polyester window material illustrated in FIG. 7.

The window film used for the transmissive windows 504 and 506 of the airway adapter of the invention must be able to handle peak airway pressures provided by ventilators to which the patient is connected. For this reason, the window film must have a tensile strength which is sufficient to withstand the peak airway pressures of the respiratory gas expired by the patient. In the aforementioned airway adapter described in U.S. Pat. No. 5,067,492, polyester is used for the $CO_2$ monitor windows because it allows the use of thinner films which absorb less energy. However, even though a thicker polypropylene film is required for comparable tensile strength to a polyester film, the long wavelength transmitting polypropylene material has been found by the present inventors to offer comparable performance. In particular, even though polypropylene films have tensile strengths which are 3 to 4 times less than that of polyester films, a thick polypropylene window which can withstand the same peak airway pressure has been found to still provide an acceptable long wavelength infrared transmission characteristic.

An airway adapter for use in an anesthetic agent analyzer in accordance with the invention will thus require selection of the proper film thickness and acceptable bonding and marking techniques. At present, a polypropylene film is preferred which can withstand an airway pressure up to at least 0.43 PSI. Of course, those skilled in the art will appreciate that other suitable films may also be used.

For maximum performance, it is also desired that the anesthetic agent detector used in accordance with the invention be thermally stable. As noted above, the six channel detector topology in accordance with a preferred embodiment of the invention provides more detector channels from the same detector area than is available with the detector described with respect to FIG. 2. The closer proximity allows for improved thermal conduction. Indeed, when measuring the thermal stability of the detector of FIGS. 4 and 5, the present inventors found that the average signal change in the same channels was approximately 3.0% in the shorter wavelength ranges, while the average signal change in the longer wavelength range was approximately 5.7%. However, those skilled in the art will appreciate that the additional change at the longer wavelengths can be partially overcome by boosting the signal or modulation at the longer wavelengths.

Those skilled in the art will also appreciate that the six channel topography should have a responsivity which is approximately 50% less than that of the three channel device illustrated in FIG. 2 because of the increased resistive shunting of the parallel opposed connection used in accordance with the invention. Despite this limitation, the present inventors have found that the detector illustrated in FIGS. 4 and 5 provides a suitable signal level which may be boosted or modulated to provide an acceptable detection level.

EXAMPLE

A prototype was constructed of a six channel anesthetic agent detector of the type illustrated in FIGS. 4 and 5. The detector was built into a capnometer sensor housing of the type illustrated in U.S. Pat. Nos. 5,081,988 and 5,095,913. The source in this housing was operated without a window to improve long wavelength energy at 7.59 volts, 1.1 watts. The airway adapter 505 in the example incorporated two 0.006 inch thick POLY IR-2 windows provided by Fresnel Technologies, Inc. The detectors were then connected to preamplifiers which were in turn connected to signal processors containing concentration calculation circuitry and a 386 microprocessor. Gas was then introduced into the airway adapter using a syringe which yielded a "no flow" condition so as to eliminate the effects of window cooling. It was found that anesthetic agents could be discriminated at long wavelengths (6–15 microns) provided suitable filters for the respective anesthetic agent gases were used.

The anesthetic agent analyzer of the present invention preferably measures the concentration of the popular anesthetic agent gases isoflurane, ethrane and halothane, although the concentrations of sivoflurane, desflurane and other new anesthetic gases may also be measured in accordance with the techniques of the invention. In order to construct such an anesthetic agent analyzer in accordance with the invention, it was necessary to find several wavelengths each of which showed selective absorption for one of the anesthetic agents. It was then necessary to find low cost infrared bandpass filters that covered those wavelengths. As known to those skilled in the art, $CO_2$ has a strong infrared absorption band in the middle infrared range centered at 4.256 microns, while $N_2O$ has a strong infrared absorption band centered at 4.54 microns. Transmission spectra for isoflurane, ethrane, and halothane, however, indicate that absorption is much stronger in the far infrared range of 6–15 microns. The transmission spectra for isoflurane, ethrane, halothane, desflurane and sivoflurane are respectively illustrated in FIGS. 10(A)–10(E). Marked on each of these figures are indications of possible absorption bands for the compounds of interest where $CO_2$ is represented by C, $N_2O$ is represented by N, the reference gas is illustrated by R, isoflurane is represented by I, ethrane is represented by E, and halothane is represented by H.

As noted above, in order to discriminate the respective anesthetic agents it is necessary to have each analytical wavelength selected such that it is absorbed by predominantly one of the three agents. Appropriate filter selection can be made in accordance with the techniques described in the aforementioned U.S. Pat. Nos. 5,081,998 and 5,095,913 and thus will not be discussed in detail herein. The inventors have found filters with bandpasses centered at approximately 8.629 microns for ethrane, 8.191 microns for isoflurane and 12.386 microns for halothane to provide suitable results.

The present inventors convolved the filter center wavelengths and half power bandwidths for each of the anesthetic agent gases with the actual gas transmission spectra of the respective anesthetic agent gases and compared the results to the actual modulations detected by the six channel detection device described in the above example. It was found by the present inventors that the actual modulation was less than predicted because of inaccuracies in the bandpass filters but that, nevertheless, enough modulation was provided for the concentrations of the respective anesthetic agents to be mathematically discriminated. Adjustments in the filter parameters are expected to bring improved results. Indeed, the present inventors have found that the key to improving modulation is the proper selection of the bandpass filters.

As known by those skilled in the art, the absorption spectra measured by a spectrometer is actually composed of many sharp peaks spaced close together called fine structure. The origin of the fine structure is in the quantum mechanics of the molecular bond energy, and it is only photon wavelengths that exactly match the fine structure that are absorbed. If the fine structure is very sharp, without much broadening, the apparent absorption over a band will be reduced. The present inventors have found that this problem may be resolved by reducing the bandwidth of the filters selected. Although this reduces signal strength, it increases modulation percentage. Narrower filters may also provide improved discrimination. Accordingly, those skilled in the art may desire to adjust the bandwidths of the filters used until signals with acceptable modulation and signal strength are achieved.

Processor 558 (FIG. 5) discriminates between the anesthetic agents by processing the signals provided from the respective detectors. In accordance with the invention, a separate concentration for each anesthetic agent is computed independently and continuously and displayed to the user of the anesthetic agent analyzer. In a preferred embodiment, processor 558 implements a polynomial or matrix equation involving terms of first and second order low/high ratios and cross product terms so as to produce separate outputs for each anesthetic agent. Unlike prior art anesthetic agent analyzers, no logical "blocking" is employed to select the "most likely" agent detected. Also, no post processing corrections are employed to modify the apparent gas concentration. Rather, the output of the anesthetic agent analyzer of the invention is a true multichannel display comparable to that from a mass spectrometer or other high quality multichannel gas monitoring instrument.

To calibrate the anesthetic analyzer of the invention, a limited set of gases are used. This set of gases comprises gases of known concentrations and a mixture of two agent gases at known concentration. Calibration is repeated for each of the different agent gas combinations. After calibration regression, the present inventors conducted a test running the calibration data back through the calibration polynomials and found standard errors for the anesthetic agent analyzer of the invention to be within an acceptable range.

In a preferred embodiment, a second order polynomial equation with cross product terms was then used to compute each agent concentration in accordance with the following equation:

$$\%Agent = A_3 C_a + A_2 C_b + A_1 C_c + A_3 A_2 C_d + A_3 A_1 C_e + A_1 A_2 C_f + A_3^2 C_g + A_2^2 C_h + A_1^2 C_i,$$

Equation 1 where:
$A_n$ = Signal from agent detector n divided by signal from reference detector n; and
$C_n$ = calibration coefficients.

The calibration coefficients $C_a - C_i$ can be readily calculated by those skilled in the art using the known calibration gases mentioned above. Accordingly, their calculation will not be described in detail herein. Of course, the polynomial equation illustrated as Equation 1 may be extended beyond three channels when more than three channels are used. Also, as will be appreciated by those skilled in the art, other equations may be used for calculating the concentrations of the respective anesthetic agent gases which take into account collision broadening and cross-talk between channels. For example, Haaland describes in an article entitled "Methods to Include Beer's Law Nonlinearities in Quantitative Spectral Analysis," *Computerized Quantitative Infrared Analysis. ASTM STP*934, G. L. McClure Editors, American Society for Testing and Materials, Philadelphia, 1987, pp. 78–94, a multivariate least-squares method for quantitative infrared analysis of multicomponent samples using nonlinear terms in the relationship between concentration and absorbance. Accordingly, the concentrations of the respective anesthetic agent gases may be calculated using the techniques described by Haaland for modeling the nonlinearity in Beer's law for quantitative spectral analysis. Of course, linear analysis may also be used to calculate the respective concentrations of the anesthetic agent gases, but such an approach is not presently preferred because of the inherent errors in a linear computation.

The present invention thus relates to an anesthetic agent analyzer which allows the discrimination of anesthetic agents using infrared absorption techniques in the far infrared (6–15 micron wavelength) range. In particular, the present inventors have found that thermopile and infrared source technology at long wavelengths up to 15 microns provide a suitable technique for discrimination of anesthetic agents and have accordingly devised a new detector topography which operates in the far infrared range to yield additional channels in the same package size with minimal complexity. The present inventors have also found that low costs plastics may be used in a disposable airway adapter for use in conjunction with the anesthetic agent analyzer of the invention so that a mainstream discriminating anesthetic agent analyzer may be used in accordance with the techniques of the invention. Also, because of the simple, lightweight configuration of the invention, a relatively small, inexpensive mainstream anesthetic agent analyzer with acceptable anesthetic agent gas modulation may be provided in accordance with the present invention.

Although an exemplary embodiment of the invention has been described in detail above, those skilled in the art will readily appreciate that many additional modifications are possible in the exemplary embodiment without materially departing from the novel teachings and advantages of the invention. For example, the present invention may be used to measure water vapor and to adjust the measured signals in accordance with the absorption of water vapor at the respective infrared detection wavelengths. For example, this may be done by selecting an additional reference wavelength at a place where water is absorbed the same as in the desired analytical band and reference the measured agent concentration to that reference. Of course, this would require additional channels in the analyzer. In addition, in order to minimize absorption caused by the accumulation of mucous and the like on the windows of the infrared airway adapter, the airway adapter windows may be coated with an anti-fog coating in accordance with the techniques described in related U.S. patent application Ser. No. 07/984,673 filed Dec. 2, 1992, also assigned to the same assignees as the present invention. Accordingly, these and all such modifications are intended to be included within the scope of the invention as defined in the following claims.

We claim:

1. A device for simultaneously measuring the concentrations of respective anesthetic agents in a respiratory gas stream, comprising:
   a source of infrared radiation;
   a separate infrared detector for each of said respective anesthetic agents, each detector disposed so as to receive incident radiation from said infrared radiation source and to produce first electrical signals representative of the received incident radiation and ambient temperature transients;
   means for directing at least a portion of said respiratory gas stream between said infrared detectors and said infrared radiation source;
   a separate reference infrared detector for each of said infrared detectors, each reference detector being connected in parallel opposed manner with its corresponding infrared detector and outputting second electrical signals representative of ambient temperature transients;
   means for shielding said reference detectors from said infrared radiation source; and
   means for processing said first and second electrical signals to produce signals representative of the concentrations of said respective anesthetic agents.

2. A device as in claim 1, wherein said infrared radiation source is a black body source having an operating temperature which is approximately 350° C. and emits a detectable amount of infrared radiation at wavelengths from 2-13 microns.

3. A device as in claim 1, further comprising an analytical filter for each of said anesthetic agents, each analytic filter passing incident infrared energy in a narrow band about an infrared frequency which is readily absorbed by the corresponding anesthetic agent to the corresponding detector.

4. A device as in claim 3, wherein said anesthetic agents comprise isoflurane, ethrane and halothane and said analytical filters comprise a filter with a narrow band about approximately a 8.2 micron wavelength for isoflurane, a filter with a narrow band about approximately a 8.6 micron wavelength for ethrane, and a filter with a narrow band about approximately a 12.4 micron wavelength for halothane.

5. A device as in claim 3, wherein said analytical filters pass infrared energy corresponding to absorption bands of anesthetic agents sivoflurane and desflurane.

6. A device as in claim 3, wherein said analytical filters pass infrared energy corresponding to absorption bands of anesthetic agents carbon dioxide and nitrous oxide.

7. A device as in claim 1, wherein said directing means comprises an airway adapter which is inserted into a patient's respiratory airway so as to receive the patient's exhaled airstream.

8. A device as in claim 7, wherein said airway adapter is formed of plastic and includes plastic windows in an optical path between said infrared detectors and said infrared radiation source.

9. A device as in claim 8, wherein said airway adapter is formed of one of a polypropylene and a polycarbonate and includes polypropylene windows in an optical path between said infrared detectors and said infrared radiation source.

10. A device as in claim 1, wherein each reference infrared detector and its corresponding infrared detector are comprised of thermopiles and are disposed back to back with said shielding means therebetween.

11. A device as in claim 1, wherein said shielding means comprises aluminum foil.

12. A device as in claim 1, wherein said processing means processes said first electrical signals D and said second electrical signals R to determine the concentration $A_X$ of three respective anesthetic agents X in accordance with the following equation:

$$A_X = A_3 C_a + A_2 C_b + A_1 C_c + A_3 A_2 C_d + A_3 A_1 C_e + A_1 A_2 C_f + A_3^2 C_g + A_2^2 C_h + A_1^2 C_i,$$

where $A_n = D_n/R_n$ and where $C_a - C_i$ are respective calibration coefficients.

13. An anesthetic agent detector for simultaneously measuring the concentrations of respective anesthetic agents in a respiratory gas stream of a patient, comprising:
   a source of infrared radiation;
   a separate infrared detector for each of said respective anesthetic agents, each detector disposed so as to receive incident radiation from said infrared radiation source and to produce first electrical signals representative of the received incident radiation and ambient temperature transients;
   means for directing at least a portion of said respiratory gas stream of said patient between said infrared detectors and said infrared radiation source;
   a separate reference infrared detector for each of said infrared detectors, each reference detector being disposed back to back with its corresponding infrared detector and connected in parallel opposed manner therewith so as to output second electrical signals representative of ambient temperature transients;
   means for shielding said reference detectors from said infrared radiation source, said shielding means being disposed between said infrared detectors and said reference detectors; and
   means for processing said first and second electrical signals to produce signals representative of the concentrations of said respective anesthetic agents.

14. A method of simultaneously measuring the concentrations of respective anesthetic agents in a respiratory gas stream of a patient, comprising the steps of:
   transmitting a beam of infrared radiation through said respiratory gas stream;
   detecting the intensity of said infrared radiation, after it has passed through said respiratory gas stream, using a separate infrared detector for each of said respective anesthetic agents, and generating first electrical signals representative of the detected infrared radiation;
   detecting ambient temperature transients in a region adjacent said infrared detectors using a separate reference infrared detector adjacent each of said infrared detectors, each reference detector being connected in parallel opposed manner with its corresponding infrared detector and being shielded from said infrared radiation, and generating second electrical signals representative of said ambient temperature transients;

generating difference signals respectively corresponding to the differences between the respective first electrical signals and second electrical signals; and processing said difference signals to produce signals representative of the concentrations of said respective anesthetic agents.

15. A method as in claim 14, wherein said transmitting step comprises the step of emitting a detectable amount of infrared radiation at wavelengths from 2–13 microns from a black body source having an operating temperature which is approximately 350° C.

16. A method as in claim 14, comprising the further steps of filtering said infrared radiation after it has passed through said respiratory gas stream using separate analytical filters for each of said anesthetic agents, each analytical filter passing incident infrared energy in a narrow band about an infrared frequency which is readily absorbed by the corresponding anesthetic agent.

17. An infrared energy detector for measuring the amount of incident infrared radiation received from a source of infrared energy, comprising:

a plurality of thermopile detectors disposed so as to receive incident radiation from said infrared radiation source via respective optical channels and to produce first electrical signals representative of the received incident radiation and ambient temperature transients;

a separate reference thermopile detector for each of said thermopile detectors, each reference thermopile detector being connected in parallel opposed manner with its corresponding thermopile detector and outputting second electrical signals representative of ambient temperature transients; and means for shielding said reference thermopile detectors from said infrared energy source.

18. A detector as in claim 17, further comprising a separate analytical filter over each of said thermopile detectors so as to form respective optical channels, each analytic filter passing incident infrared energy in a narrow band about an infrared frequency which is readily absorbed by a particular gas component with a characteristic absorption band centered about said infrared frequency.

19. A detector as in claim 17, wherein each reference thermopile detector and its corresponding thermopile detector are comprised of thermopiles which are disposed back to back with said shielding means therebetween.

20. A detector as in claim 19, wherein said shielding means comprises aluminum foil.

* * * * *

UNITED STATES PATENT AND TRADEMARK OFFICE
CERTIFICATE OF CORRECTION

PATENT NO. : 5,296,706
DATED : March 22, 1994
INVENTOR(S) : Braig et al.

It is certified that error appears in the above-identified patent and that said Letters Patent is hereby corrected as shown below:

Column 1, line 48, change "$(N_2\ 0)$" to --$(N_2O)$--.

Column 6, line 50, change "$A_3A_1C_ee$" to --$A_3A_1C_e$--.

Column 6, line 51, change "$-IA_2C_f$" to --$A_1A_2C_f$--.

Column 7, line 3, after "adjacent" add --to--.

Column 10, line 65, change "Mylar TM" to --Mylar™--.

Column 11, line 48, change "Mylar TM" to --Mylar™--.

Column 15, line 63, change "$A_1^2C_1$" to --$A_1^2C_i$--.

Column 18, line 61, after "adjacent" insert --to--.

Signed and Sealed this

Twenty-third Day of August, 1994

Attest:

BRUCE LEHMAN

*Attesting Officer*     *Commissioner of Patents and Trademarks*